United States Patent [19]

Brownscombe

[11] Patent Number: 4,992,613

[45] Date of Patent: Feb. 12, 1991

[54] DOUBLE-BOND ISOMERIZATION PROCESS USING BASIC ZEOLITE CATALYSTS

[75] Inventor: Thomas F. Brownscombe, Houston, Tex.

[73] Assignee: Shell Oil Company, Houston, Tex.

[21] Appl. No.: 394,693

[22] Filed: Aug. 16, 1989

[51] Int. Cl.$^5$ .............................................. C07C 5/23
[52] U.S. Cl. ................................................... 585/666
[58] Field of Search ........................................ 585/666

[56] References Cited

U.S. PATENT DOCUMENTS 3,697,616 10/1972 McDonough et al. ............. 585/666
4,140,726 2/1979 Unland et al. .................. 260/668 B

OTHER PUBLICATIONS

Barthomeuf et al., "Basicity and Basic Properties of Zeolites, Materials Chemistry and Physics", 18 (1988) 553-575.
Martens et al., "Sodium Clusters in Large Pore Zeolites as Basic Catalysts".
Rabo et al., "Studies of Cations in Zeolites".
Martens et al., "Preparation and Catalytic Properties of Ionic Sodium Clusters in Zeolites", Nature, 315, 568-570 (1985).
Yoon et al., "Novel Synthesis of Ionic Clusters ($Na_4^{3+}$) in Zeolites, " J. Chem. Soc., Chem. Commun., 510-511 (1988).
Harrison et al., "Ionic and Metallic clusters of the Alkali Metals in Zeolite Y," J. Solid State Chem., 54, 330-341 (1984).
Martens et al., "Sodium Clusters in Zeolites as Active Sites for Carbanion Catalyzed Reactions".
Englehardt et al., "Alkylation of Toluene with Methanol on Commercial X Zeolite in Different Alkali Cation Forms", J. Cat., 107, 196-306 (1987).
Hathaway et al., "Base Catalysis by Alkali-Modified Zeolite", J. Cat., 116,263-284 (1989).

*Primary Examiner*—Curtis R. Davis

[57] ABSTRACT

This invention relates to a process for the double bond isomerization of an olefin which comprises contacting said olefin with a catalyst comprising zeolite and an alkali(ne earth) metal compound wherein the sum of the amount of the alkali(ne earth) metal in the compound plus any metal cation exchanged into the zeolite is in excess of that required to provide a fully metal cation-exchanged zeolite.

32 Claims, No Drawings

DOUBLE-BOND ISOMERIZATION PROCESS USING BASIC ZEOLITE CATALYSTS

FIELD OF THE INVENTION

This invention relates to an olefin double-bond isomerization process using a basic zeolite catalyst.

BACKGROUND OF THE INVENTION

Double bond isomerization is a reaction catalyzed by basic and acidic catalysts. Basic catalysts are normally more selective, since they do not generate cations which can undergo skeletal isomerizations. The instant catalysts are particularly useful for double bond isomerization.

NaY zeolite itself is reported in the literature to catalyze cracking processes by a radical mechanism. The cracking observed along with isomerization by NaY zeolite is largely consistent with the reported radical mechanism, perhaps with a contribution from weak acid sites. When NaY zeolite and CaA zeolites are converted to the instant catalysts, the resulting products lose their cracking activity.

The instant catalysts are thus particularly useful for the isomerization of additive range ($C_4$ to $C_8$) olefins and detergent range ($C_{10}$ to $C_{18}$) olefins, although higher range olefins can be isomerized.

Isomerized olefins serve as feedstocks for the chemical industry. Such olefins can be converted to corresponding alcohols or aldehydes. Higher molecular weight alcohols can further be ethoxylated with ethylene or propylene oxide in the presence of a catalyst to form conventional detergents while lower molecular weight alcohols can be esterified with aromatic acids to form plasticizers.

Olefins in the presence of a double bond isomerization catalyst and when given sufficient time at reaction temperature will isomerize to an equilibrium distribution. For example, alpha olefins will isomerize to an equilibrium mixture of internal olefins. However, when shape selective double bond isomerization catalysts are used, such as the instant zeolite catalysts, olefin product mixtures can be obtained that differ from an equilibrium mixture.

The term "alkali(ne-earth) metal" as used hereinafter refers to a metal selected from the group consisting of alkali metal, alkaline earth metal and mixtures thereof, that is, it refers to alkali metal and/or alkaline earth metal and includes one or more alkali metals, one or more alkaline earth metals and two or more of a mixture of alkali metal(s) and alkaline earth metal(s).

SUMMARY OF THE INVENTION

This invention relates to a process for the double bond isomerization of an olefin which comprises contacting said olefin with a catalyst comprising a zeolite and an alkali metal and/or an alkaline earth metal compound wherein the sum of the amount of the alkali metal and/or alkaline earth metal in the compound plus any metal cation exchanged into the zeolite is in excess of that required to provide a fully metal cation-exchanged zeolite. In a preferred embodiment the catalyst is prepared by impregnating a zeolite with a solution of an alkali metal salt and/or alkaline earth metal salt wherein said alkali metal and/or alkaline earth metal impregnated in the zeolite is in excess of that required to exchange out the ion exchangable sites present in the zeolite, drying the resultant impregnated material and then calcining the resultant composition. Preferred zeolite-alkaline earth metal compound catalysts are prepared by impregnating a zeolite with a soluble alkaline earth metal salt, followed by precipitation of an insoluble alkaline earth metal compound by contacting the impregnated zeolite with a precipitating agent, such as ammonium hydroxide.

DETAILED DESCRIPTION OF THE INVENTION

Isomerization Process

This instant invention provides a process for shifting the double bond of an olefin by contact with an isomerization catalyst. Isomerization is carried out in a gas or liquid phase at isomerization conditions. Isomerization conditions typically include a temperature in the range of from about 0° C. to about 500° C., preferably from about 100° C. to about 150° C., a pressure in the range of from about 1 psig to about 2000 psig, preferably from about atmospheric (15 psig) to about 2000 psig and a weight hourly space velocity in the range of from 0.1 to about 20. The olefins to be isomerized may be a pure olefin feedstock or may be suitably diluted with an inert organic diluent such as an alkane or aromatic compound.

The Catalyst

The catalysts that are utilized in the process are described in co-pending U.S. patent applications Ser. Nos. 354,586, filed June 22, 1989 and 387,265, filed July 31, 1989, incorporated by reference herein.

Essentially any crystalline zeolitic aluminosilicate can be employed to prepare the catalysts utilized in the instant process. The zeolites can include both synthetic and naturally occurring zeolites. Illustrative of the synthetic zeolites are Zeolite X, U.S. Pat. Nos. 2,882,244; Zeolite Y, 3,130,007; Zeolite A, 2,882,243; Zeolite L, Bel. No. 575,117; Zeolite D, Can. No. 611,981; Zeolite R, U.S. Pat. Nos. 3,030,181; Zeolite S, 3,054,657; Zeolite T, 2,950,952; Zeolite Z, Can. No. 614,995; Zeolite E, Can. No. 636,931; Zeolite F, U.S. Pat. Nos. 2,995,358; Zeolite O, 3,140,252; Zeolite W, 3,008,803; Zeolite Q, 2,991,151; Zeolite M, 2,995,423; Zeolite H, 3,010,789; Zeolite J, 3,001,869; Zeolite W, 3,012,853; Zeolite KG, 3,056,654; Zeolite SL, Dutch No. 6,710,729; Zeolite Omega, Can. No. 817,915; Zeolite ZK-5, U.S. Pat. Nos. 3,247,195; Zeolite Beta, 3,308,069; Zeolite ZK-4, 3,314,752; Zeolite ZSM-5, 3,702,886; synthetic mordenite; the so-called ultrastable zeolites of U.S. Pat. Nos. 3,293,192 and 3,449,070; and the references cited therein, incorporated herein by reference. Other synthetic zeolites are described in the book "Zeolite Molecular Sieves-Structure, Chemistry and Use," by Donald W. Breck, 1974, John Wiley & Sons, incorporated by reference herein. Illustrative of the naturally occurring crystalline zeolites are analcime, bikitaite, edingtonite, epistilbite, levynite, dachiardite, erionite, faujasite, analcite, paulingite, noselite, ferrierite, heulandite, scolecite, stilbite, clinoptilolite, harmotone, phillipsite, brewsterite, flakite, datolite, chabazite, gmelinite, cancrinite, leucite, lazurite, scolecite, mesolite, ptilolite, mordenite, nepheline, natrolite, scapolite, thomsonite, gismondine, garronite, gonnardite, heulandite, laumontite, levynite, offretite, yugawaralite. Descriptions of certain naturally occurring zeolites are found in the aforementioned book by Breck, in the book "Molecular Sieves-Principles of Synthesis and Identification", R. Szostak, Van Nostrand Reinhold, New York, 1989, both incorporated by reference herein, and in other known references. These zeolites may be in the hydrogen form or may be partially or fully exchanged with ammonium or metal ions.

As used herein, the term "compound" as applied to alkali(ne-earth) metal refers to the combination of alkali(ne-earth) metal with one or more elements by chemical and/or physical and/or surface bonding, such as ionic and/or covalent and/or coordinate and/or van der Waals bonding, but specifically excludes that bonding involved between an alkali(ne-earth) metal and a zeolite when such alkali(ne-earth) metal is located in a cation exchange site of the zeolite. The term "ionic" or "ion" refers to an electrically charged moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions. The term "oxidic" refers to a charged or neutral species wherein an element such as an alkali(ne-earth) metal is bound to oxygen and possibly one or more different elements by surface and/or chemical bonding. This, an oxidic compound is an oxygen-containing compound, which also may be a mixed, double, or complex surface oxide. Illustrative oxidic compounds include, by way of non-limiting example, oxides (containing only oxygen as the second element), hydroxides, nitrates, sulfates, carboxylates, carbonates, bicarbonates, oxyhalides, etc, as well as surface species wherein the alkali(ne-earth) metal is bound directly or indirectly to an oxygen either in the substrate or the surface. "Surface" as applied to zeolites and the instant catalysts refers to external surface as well as the internal pore surface, the internal surface being both the surface of the macro pores resulting from the agglomeration of individual particles or crystallites as well as the surface of the mesopores and micropores and supercages that result from the intrinsic zeolite crystal structure. The term "salt" as used in the instant specification and claims is meant to encompass a single salt as well as mixtures of two or more salts. The term "alkali metal" is used herein as a descriptor of the elements of Group IA of the Periodic Table of the Elements (Li, Na, K, Rb, Cs, Fr). The term "alkaline earth metal" is used herein as a descriptor of the elements of Group IIA of the Periodic Table of the Elements (Be, Mg, Ca, Sr, Ba, Ra). Alkali(ne-earth) metal herein does not refer to the element in the metallic or zero valent state, but rather is a shorthand use for the element in the positive valent state, that is, it will be understood to be combined as a salt, compound, complex, etc. The term "basic" refers to having the characteristic of a base; e.g., when placed in a solution, a basic material will have a pH consistent with a base rather than an acid and, if a catalyst, will catalyze chemical reactions that are catalyzed by bases.

The alkali(ne-earth) metal salts that are suitable for preparing the catalysts utilized in the instant process are any salts that can be dissolved in a suitable impregnating solution or which can be melted to form their own impregnating solution or which can be sublimed and condensed on the zeolite. Illustrative but non-limiting examples of suitable salts are alkali(ne-earth) metal bicarbonates, carbonates, chlorates, perchlorates, cyanides, hydroxides, iodates, nitrates, nitrites, sulfates, hydrogen sulfates, sulfites, dithionates, thiosulfates, alkoxides, carboxylates, sulfonates, iodates, halides and the like. Of the alkali(ne-earth) salts that can be utilized in the instant invention, the hydroxide salts, particularly of alkali metals, are less preferred since these strongly basic salts in high concentrations can contribute to a degradation of the crystallinity of the zeolite. Salts which can be solubilized in a suitable solution are preferred. Preferred salts are those which have an oxygen-containing anion or oxyanion or which can be precipitated in situ with oxyanion. Useful salts are those which decompose at least in part upon calcination in the presence of the zeolite to provide an alkali(ne-earth) metal-oxygen-containing moiety (e.g., Na-O-, Ca-O-, etc.), that is, produce an oxidic compound. When the alkali(ne-earth) metal salt is associated with an anion which does not contain oxygen it is necessary that the salt be precipitated in situ with a suitable oxyanion, or alternatively, after impregnation, the subsequent calcination is carried out in an oxygen-containing atmosphere to cause the salt to react with the oxygen to provide the alkali(ne-earth) metal-oxygen-containing moiety, that is, produce an alkali(ne-earth) metal oxidic compound. Decomposition can be indicated by the evolution of gases such as carbon oxides, nitrogen oxides, sulfur oxides etc. Decomposition will also be indicated by disappearance at least in part of the particular anionic form associated with the alkali(ne-earth) metal in the impregnation liquid. For example, when carboxylates and alkoxides are calcined the carboxylate and alkoxide moiety associated with the alkali(ne-earth) metal will decompose giving off carbon oxides and/or water and/or hydrocarbons, thereby disappearing at least in part. Particularly preferred salts to be used in an impregnating solution are (alkali) carbonates nitrates and carboxylates. Mixtures of alkali(ne-earth) metal salts, that is, two or more salts with differing anions, differing cations or differing anions and cations can be utilized to prepare the impregnated zeolite.

One method that can be used to prepare the catalysts utilized in the instant process involves the use of molten alkali(ne-earth) metal salt to impregnate the zeolite. In this method a suitable salt, that is, one melting below about 850° C., is melted and the zeolite is added to the molten salt or the molten salt is added to the zeolite causing the molten salt to impregnate the pores of the zeolite. A very suitable impregnation technique is to utilize that amount of molten salt that is equal to or less than that amount of molten salt that will just fill the pores of the zeolite. Alternatively, zeolite particles can be immersed in a molten salt bath to cause impregnation of the molten salt into the zeolite followed by separation of the excess molten salt from the zeolite, say by filtration, centrifugation or washing. Alternatively, zeolite particles can be coated with finely divided particles of a suitable alkali(ne-earth) metal salt and heated to above the melting point of the salt, causing the molten salt to impregnate the pores of the zeolite. Many other methods, such as fluid bed impregnation or spraying molten salt or solid salt onto zeolite in a rotating kiln will be obvious to one skilled in the art. After impregnation, the impregnated zeolite is calcined to produce the catalyst utilized in the instant process. The calcining temperature may be the same or lower than the impregnating temperature but frequently it is higher. Drying is not required when the molten salt technique is utilized, but may be utilized to remove residual water remaining in the zeolite. The impregnation and calcination can be carried out in one continuous step or sequence. The alkali(ne-earth) metal nitrates and carboxylates are particularly suitable for use in the molten impregnation method.

Another method is to use a sublimable alkali(ne-earth) metal salt. In this method a suitable salt is sublimed at above its sublimation temperature to produce a vaporous salt and the resulting vapor is contacted with the zeolite maintained at a temperature near or below the sublimation temperature of the salt thereby causing the vapor to condense upon and within the pores of the zeolite thereby impregnating it. Calcination follows to prepare the catalysts utilized in the instant process. Drying before calcination is not required in this case, but may be utilized to remove residual water in the zeolite. The impregnation and calcination can be carried out in one continuous step or sequence.

Most conveniently and preferably, solutions of alkali(ne-earth) metal salts are used to impregnate the zeolites. The solvents utilized to dissolve the salts may be organic or inorganic. The only requirement is that the desired salt be soluble in the particular solvent. Hydroxylic solvents are preferred. Water is a particularly preferred solvent. The lower alkanols are also particularly suitable for use with salts having strong basicity in water in order to minimize base-zeolite structure interactions during the impregnation process. Organic solvents are particularly useful as solvents for alkali(ne-earth) metal salts which have organic ionic components such as carboxylate, sulfonate, alkoxide, etc. Organic solvents are also useful for inorganic alkali(ne-earth) metal salts. Alkaline earth metal salts having a low solubility in an organic solvent can be used with that solvent to provide small, but well controlled amounts of alkali(ne-earth) metal to the zeolite while minimizing solvent-base-zeolite structure interactions. Illustrative, but non-limiting examples of organic solvents include alcohols, including polyhydric alcohols, ethers, esters, ketones, amides, sulfoxides and chloro/fluorohydrocarbons such as the various freons. Specific illustrative examples include methanol, ethanol, glycol, dimethyl ether, methyl acetate, methylethyl ketone, dimethyl formamide ("DMF"), dimethyl sulfoxide ("DMSO"), N-methyl pyrrolidone ("NMP"), hexamethylphosphoramide ("HMPA"), dichlorodifluoromethane, methyl chloride, ethylene dichloride, ethylene carbonate, etc. Illustrative, but non-limiting examples of inorganic solvents include water, liquid ammonia, liquid carbon dioxide, liquid sulfur dioxide, carbon disulfide, carbon tetrachloride, etc. Mixtures of solvents which are mutually miscible may be utilized.

When the catalyst comprises a zeolite-alkaline earth metal compound, a preferred variation on the impregnation technique comprises impregnating the zeolite with a soluble salt of an alkaline earth metal salt, followed by contact or reimpregnation with a precipitating agent, such as a suitable solubilized anion, that will form a precipitate in situ with alkaline earth metal ion. For example, a zeolite is first impregnated with an aqueous solution of barium or calcium nitrate or chloride. Then the impregnated zeolite, without intermediate drying and/or calcining is contacted with an aqueous solution of ammonium sulfate or hydroxide, causing barium or calcium sulfate or hydroxide to precipitate within the zeolite. This resultant material is then dried as necessary and optionally calcined. Gaseous precipitating agents may also be utilized. For example, after a zeolite is first impregnated with an aqueous solution of alkaline earth metal nitrate, it is then contacted with or without intermediate drying with gaseous ammonia or dimethylamine, resulting in the precipitation of or conversion to the alkaline earth metal hydroxide. Preferred precipitating agents are those which produce an oxidic compound or a compound which is converted to an oxidic compound upon calcination.

Single or multiple impregnations may be used. When multiple impregnations are used intermediate drying steps, optionally followed by precipitation and/or calcination may be utilized. Generally any amount of impregnating liquid can be used in the impregnation process. For example, the zeolite can be dipped into a large excess (compared to the pore volume of the zeolite), removed and shaken of excess liquid. Alternatively, an amount of impregnating liquid considerably less than the pore volume can be sprayed onto an agitated bed of zeolite. For purposes of economy, control and other reasons, the volume of impregnating liquid will preferably range from about the pore volume to about four or five times, preferably about twice the pore volume of the zeolite to be impregnated. Alternatively, a "dry" impregnation technique is utilized wherein just that amount of impregnating solution is used which will just fill the pores of the zeolite. In another embodiment, baskets of zeolite material are dipped into a vat of impregnating solution, removed, dried and optionally calcined.

The concentration of alkali(ne-earth) metal salts in the impregnating solution is not critical and is selected, inter alia, on the basis of the zeolite used, the amount of ion exchange capacity present in the zeolite, the degree of basicity of the final product desired, the impregnation solvent used and the type of impregnation utilized, that is, multiple or single. Concentrations of alkali(ne-earth) metal salt(s) in the impregnating solution will typically range from about 0.01 moles per liter to the solubility limit of the salt(s). A suitable range is from about 0.01 to about 20 moles per liter, more preferably from about 0.1 to about 10 moles per liter.

The amount of alkali(ne-earth) metal which is impregnated into the zeolite must be in excess of that which would provide a fully cation-ion exchanged zeolite. For example, if the starting zeolite were completely in the hydrogen form and had an ion exchange capacity of 12% (basis $Na_2O$), then the equivalent amount of alkali(ne-earth) metal impregnated (basis $Na_2O$) must exceed the 12%. If the starting zeolite were one which had already been 80% exchanged with a metal cation, the amount of alkali(ne-earth) metal to be added by impregnation would be in excess of that amount required to exchange the remaining 20%. If the starting zeolite were fully metal cation exchanged, then any amount of alkali(ne-earth) metal in the impregnating solution would suffice. It is to be understood that impregnation of a partially or fully cation-exchanged zeolite will most likely result in some counter ion exchange between the impregnating alkali(ne-earth) metal cation(s) and the cations already present in the zeolite, but the resulting catalyst will still be within the scope of the instant invention in having an excess of alkali(ne-earth) metal present over the amount exchanged into the fully exchanged zeolite. When the amount of impregnating solution that is utilized is such that after impregnation no excess solution is removed, then the amount of alkali(ne-earth) metal salt in the impregnating solution will be the same as the amount impregnated into the zeolite. When an amount of impregnating solution is used that requires that an excess amount of solution must be removed, for example, by filtration or centrifugation, from the impregnated zeolite after impregnation, then the amount of alkali(ne-earth) metal in the impregnating solution will exceed the amount of alkali(ne-earth) metal impregnated into the zeolite. In this latter case, the amount of alkali(ne-earth) metal impregnated into the zeolite can be determined by a knowledge of concentration of alkali(ne-earth) metal in the impregnating solution before the impregnation, the concentration of alkali(ne-earth) metal in the excess solution removed from the impregnated zeolite and the amount of solution remaining after impregnation (the excess). Alternatively, the impregnated zeolite can be analyzed for alkali(ne-earth) metal content.

The catalysts utilized in the instant process which comprise a zeolite and an alkali(ne-earth) metal compound can be divided into four somewhat arbitrary classes, depending on the amount of alkali(ne-earth) metal compound that is present in the catalyst. In order of increasing basicity, there are low base, low-intermediate base, high-intermediate base and high base catalysts. The higher the basicity of the instant catalysts, the higher will be the suppression of any acid function of the zeolite. The calculations of the ranges and limits for these various classes are to be made considering the alkali(ne-earth) metal as the metal (ion) and any metal(s) exchanged into the zeolite as the (ionic) equivalent of an alkali(ne-earth) metal.

When considering as a basis for calculation the zeolite having no cations exchanged therein, the low base catalysts will have the sum of the alkali(ne-earth) metal in the alkali(ne-earth) metal compound and any metal cation exchanged into the zeolite ranging from greater than to about 1.2 times the amount required to provide a fully cation-exchanged zeolite (or times the exchange capacity). When considering the fully cation-exchanged zeolite as a basis for calculation, the amount of alkali(ne-earth) metal in the alkali(ne-earth) metal compound is greater than to about 0.2 times the amount of alkali(ne-earth) metal that would be required to provide a fully metal cation-exchanged zeolite (or times the exchange capacity).

When considering as a basis for calculation the zeolite having no cations exchanged therein, the low-intermediate base catalysts will have the sum of the alkali(ne-earth) metal in the alkali(ne-earth) metal compound and any metal cation exchanged into the zeolite ranging from about 1.2 to about 1.5 times the amount required to provide a fully cation-exchanged zeolite (or times the exchange capacity). When considering the fully cation-exchanged zeolite as a basis for calculation, the amount of alkali(ne-earth) metal in the alkali(ne-earth) metal compound ranges from about 0.2 to about 0.5 times the amount of alkali(ne-earth) metal that would be required to provide a fully metal cation-exchanged zeolite (or times the exchange capacity).

When considering as a basis for calculation the zeolite having no cations exchanged therein, the high-intermediate base catalysts will have the sum of the alkali(ne-earth) metal in the alkali(ne-earth) metal compound and any metal cation exchanged into the zeolite ranging from about 1.5 to about 2 times the amount required to provide a fully cation-exchanged zeolite (or times the exchange capacity). When considering the fully cation-exchanged zeolite as a basis for calculation, the amount of alkali(ne-earth) metal in the alkali(ne-earth) metal compound ranges from 0.5 to about 1 times the amount of alkali(ne-earth) metal that would be required to provide a fully metal cation-exchanged zeolite (or times the exchange capacity).

When considering as a basis for calculation the zeolite having no cations exchanged therein, the high base catalysts will have the sum of the alkali(ne-earth) metal in the alkali(ne-earth) metal compound and any metal cation exchanged into the zeolite ranging from about 2 times the amount required to provide a fully cation-exchanged zeolite (or times the exchange capacity) to the limit of alkali(ne-earth) metal compound that can be physically impregnated into the zeolite, which in a preferred embodiment is about 3.5 times the amount required to provide a fully cation-exchanged zeolite (or times the exchange capacity). When considering the fully cation-exchanged zeolite as a basis for calculation, the amount of alkali(ne-earth) metal in the alkali(ne-earth) metal compound ranges from about 1 times the amount of alkali(ne-earth) metal that would be required to provide a fully metal cation-exchanged zeolite (or times the exchange capacity) to the limit of alkali(ne-earth) metal compound that can be physically impregnated into the zeolite, which in a preferred embodiment is about 2.5 times the amount required to provide a fully cation-exchanged zeolite (or times the exchange capacity).

In general it is preferred to have a slight excess of alkali(ne-earth) metal present. When considering as a basis for calculation the zeolite having no cations exchanged therein, the preferred catalysts will have the sum of the alkali(ne-earth) metal in the alkali(ne-earth) metal compound and any metal cation exchanged into the zeolite being greater than 1, preferably greater than about 1.05, more preferably greater than about 1.1, even more preferably greater than about 1.15, even more preferably greater than about 1.2, even more preferably greater than about 1.5, even more preferably greater than about greater than about 2 times the amount required to provide a fully cation-exchanged zeolite (or times the exchange capacity). When considering the fully cation-exchanged zeolite as a basis for calculation, the amount of alkali(ne-earth) metal in the alkali(ne-earth) metal compound is greater than zero, preferably greater than about 0.05, more preferably greater than about 0.1, even more preferably greater than about 0.15, even more preferably greater than about 0.2, even more preferably greater than about 0.5, and even more preferably greater than about 1 times the amount of alkali(ne-earth) metal that would be required to provide a fully metal cation-exchanged zeolite (or times the exchange capacity).

When considered in terms of those cases where increasing basicity is desired, and when considered in terms of the non-cation exchanged zeolite as a basis for calculation, the sum of alkali(ne-earth) in the alkali(ne-earth) metal compound and any metal cation exchanged into the zeolite is greater than about 1.2, more preferably greater than about 1.5 and even more preferably greater than about 2 times the amount required to provide a fully cation-exchanged zeolite (or times the exchange capacity). When considering the fully cation-exchanged zeolite, the amount of alkali(ne-earth) metal in the alkali(ne-earth) metal compound is greater than about 0.2, more preferably greater than about 0.5, and even more preferably greater than 1 times the amount of alkali(ne-earth) metal that would be required to provide a fully metal cation-exchanged zeolite.

After impregnation utilizing an impregnating solution or a subsequent precipitating solution, the impregnated zeolite is dried to remove the solvent of the impregnating and/or precipitating solution. The drying conditions are not critical to the instant invention. Drying may be carried out at atmospheric pressure, superatmospheric pressure or under vacuum. It also may be carried out by passing a dry (with regard to the impregnating solvent) gas over a bed of the zeolite. Drying temperatures will depend upon the solvent used. For those solvents that are liquid at low temperatures, such as liquid carbon dioxide or liquid sulfur dioxide, the drying temperature can be relatively low, that is, below room temperature. For the more conventional solvents which are liquid at or above room temperature, higher temperatures will be used. For these solvents temperatures will typically range from about room temperature to about 200° C. In most cases drying temperatures will be less than about 200° C., preferably less than 150° C. Drying times are dependent upon the drying temperature and pressure, typically from about one minute to about twenty hours, although longer or shorter times can be utilized. Drying atmospheres and pressures are normally not critical. The drying atmosphere may be neutral, oxidizing, reducing or a vacuum.

After drying to remove an impregnating solvent or after impregnation by means of a molten or vaporous salt, the impregnated zeolite is optionally calcined at elevated temperatures. Calcination conditions will range from about 150° C. to about 850° C., preferably from about 200° C. to about 750° C., and more preferably from about 200° C. to about 600° C. Calcining times are dependent on the calcining conditions selected and typically range from about one minute to about twenty hours, although longer or shorter times can be utilized. Calcining conditions and times are also adjusted according to the thermal stability. Calcination conditions should not be so extreme as to cause extreme loss of zeolite crystallinity. Calcining atmospheres may be neutral, oxidizing or reducing. When the impregnating salt has an anionic component which does not contain oxygen, an oxygen-containing calcining atmosphere is preferably utilized. Neutral atmospheres such as provided by nitrogen and oxidizing atmospheres such as provided by air are preferred.

In a preferred embodiment when using an impregnation or an impregnating/precipitating solution, the drying and calcining steps are combined into one integrated process step. In this combined step the impregnated zeolite is heated through the lower temperatures at a rate slow enough that physical disruption of the zeolite does not occur due to rapid volatilization of the solvent from the impregnation. After the solvent has been removed, the zeolite is then heated to the desired calcining temperature, maintained for the desired calcining time and then cooled to room temperature. Calcining (and drying) can be carried out in situ during the operation of a catalytic process in a catalytic reactor.

The exact form of the alkali(ne-earth) metal after calcination is not know. Without intending to limit the scope of the instant invention, it is believed that the alkali(ne-earth) metal(s) is present as one or more alkali(ne-earth) metal oxidic compounds. It is speculated that the alkali(ne-earth) metal compound(s) are probably in the form of a surface oxide or multiple surface oxides with the zeolite, in particular with the aluminum and/or silicon and/or oxygen of the zeolite lattice, possibly in combination with species contained in or formed from the impregnation solution or during the calcination process.

The calcination contributes to the production of a catalyst which is basic and this basic nature is thought to derive from the particular nature of the alkali(ne-earth) metal compound present after calcination. However, those catalysts produced by precipitation with a basic precipitating agent are within the scope of the instant invention, even without calcination taking place. The basic nature of these materials can be seen from the fact that instant catalysts when placed in a solvent produce effects that are basic rather than acidic in nature. This can been seen by the use of suitable chemical or electrochemical indicators.

The basicity of the instant catalysts can be determined in various ways. For example, it can be determined by measuring the extent to which various base-catalyzed reactions are carried out in the presence of of the instant catalysts. Another method is to place the instant catalyst in a solvent and measure the resulting pH by use of chemical or electrochemical indicators. A specific example would involve placing 20 mg of catalyst in 2 g of water and using a pH meter or pH paper to measure the resulting pH. Another method is to use various indicators in non-aqueous solutions and compare the indicator response caused by the instant catalysts with the indicator response caused by selected reference samples. Suitable indicators are 4-nitroaniline or 4-chloroaniline dissolved in dimethyl sulfoxide ("DMSO") or benzene (@0.1 g/cc). Examples of indicator responses with various reference samples is shown in Table 1 below.

TABLE 1

| Reference | 4-nitroaniline/DMSO | 4-chloroaniline/benzene |
| --- | --- | --- |
| NaNH$_2$ | very dark blue | purplish brown |
| KOH | dark blue | cream |
| NaY-Zeolite | yellow | cream |
| amorphorous SiO$_2$ | faint yellow | cream |

In general terms the catalysts utilized in the instant process comprise a basic, structured, that is a zeolitically structured, alkali(ne-earth) metal-containing aluminosilicate containing in compound form an excess of alkali(ne-earth) metal over that necessary to provide a fully metal cation-exchanged aluminosilicate. More specifically, the instant catalysts comprise a zeolite and an alkali(ne-earth) metal compound, particularly an oxidic compound, wherein the sum of the amount of the alkali(ne-earth) metal in the compound plus any metal cation exchanged into the zeolite is in excess of that required to provide a fully metal cation-exchanged zeolite. The instant catalysts will contain at least a portion of their pore volume in micropores in the range of from about three to about twelve angstroms. The instant catalysts react as bases when placed in solvents and catalyze base-catalyzed reactions. In a preferred embodiment for shape selective catalysis, the alkali(ne-earth) metal compound is substantially located on the internal pore surfaces of the zeolite rather than the external surfaces.

The instant catalysts retain at least a portion of a crystalline zeolite structure. The term "crystalline" is employed herein to designate an ordered structure capable of being detected by electrooptical or diffraction techniques, normally by X-ray diffraction, giving a consistent crystallographic pattern. Such an ordered structure can persist even after some of the structural silica or alumina is removed from the crystal lattice, as by leaching with acids, or with bases such as might occur during the impregnation process, or by other physical or chemical methods. Sometimes the ordered structure may become so attenuated by these or other means as to fail to diffract X-rays, but in such cases other electrooptical methods, such as electron beam diffraction may be utilized. In other cases the crystallite size may become so small that diffraction effects may become so diffuse that the amount of crystalline structure may be difficult to detect or determine. In this latter instance, however, the retention of a large surface area after chemical and/or physical processing will indicate the retention of a certain amount crystalline zeolite structure. Thus these latter materials are still structured aluminosilicates as opposed to amorphous aluminosilicates and are within the scope of the instant invention.

The catalysts utilized in the instant process, alone or in combination with other catalytic components, may be distributed throughout an inert inorganic diluent which also may serve as a binder. Non-limiting examples of such diluents include aluminas, silicas, silica-aluminas, charcoal, pumice, magnesia, zirconia, keiselguhr, fullers' earth, silicon carbide, clays and other ceramics. In a preferred use of binders the instant zeolitic catalysts are intimately mixed a finely divided, hydrous, refractory oxide of a difficulty reducible metal. The term "hydrous" is used to designate oxides having structural surface hydroxyl groups detectable by infrared analysis. The preferred oxides are alumina, silica, magnesia, beryllia, zirconia, titania, thoria, chromia, and combinations thereof such silica-alumina, silica-magnesia, and the like. Naturally occurring clays comprising silica and alumina may also be utilized, preferably after acid treatment. The metal oxide can be combined with the instant catalysts as a hydrous sol or gel, an an anhydrous activated gel, a spray dried powder or a calcined powder. In one modification a sol or solution of the metal oxide precursor such as an alkali(ne-earth) metal silicate or aluminate can be precipitated to form a gel in the presence of the catalysts utilized in the instant process. When less hydrous forms of the metal oxide are combined with the instant catalysts, essentially any method of effecting intimate admixture of the components may by utilized. One such method is mechanical admixture, e.g., mulling, which involves admixing the instant catalysts in the form of a powder with the slightly hydrous, finely divided form of the metal oxide. The diluent or binder may be added to the instant catalysts at any point in their preparation, that is, before, during or after impregnation, drying and/or calcination.

The instant catalysts may also be further activated by the incorporation into the zeolite of additional alkali metal compounds or salts, followed by calcination. For example a catalyst utilized in the instant process may be impregnated by an aqueous solution of an alkali metal carbonate, dried and calcined to provide an enhanced basic catalyst.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The following illustrative embodiments are provided for illustration and are not to be construed as limiting the invention.

ILLUSTRATIVE EMBODIMENT I

Catalyst Preparation

The catalysts utilized were prepared as follows:

I. Comparative NaY Zeolite

Baylith CP-190 NaY zeolite (straight out of the can) was calcined at 500° C. for one hour in flowing nitrogen.

II. Low Base Composition

Baylith CP-190 NaY zeolite was dried in a 100° C. vacuum oven for 16 hrs. 125 Grams of this dried NaY zeolite was impregnated with 4.81 g of potassium carbonate (MCB ACS reagent) dissolved in 62.4 cc of deionized water. The zeolite was mixed in a dish during impregnation and then dried 16 hrs in a 100° C. vacuum oven. This dried material was calcined at 550° C. for 55 minutes in flowing nitrogen. This material contained about 1.8 equivalents of potassium per zeolite supercage.

III. High Base Composition

Baylith CP-190 NaY zeolite was dried in a 100° C. vacuum oven for 16 hrs. 61.7 Grams of this dried NaY zeolite was impregnated with 36.53 g of potassium carbonate (MCB ACS reagent) dissolved in 61 cc of deionized water. The zeolite was mixed in a dish during impregnation and then dried 66 hrs in a 100° C. vacuum oven. The dried zeolite was pressed in bags in an isostatic press at 20,000 psi for 2 minutes. It was then ground and sieved to 16-30 mesh particles. These particles were calcined at 550° C. for one hour in flowing nitrogen. This material contained about 20 equivalents of potassium per zeolite supercage.

Catalyst Testing

Isomerization catalysts were tested in a stainless steel flow reactor measuring 14.75" in length and 0.625" in internal diameter. The reactor was packed bottom to top as follows: a small wad of glass wool, 33 cc of catalyst, a small wad of glass wool, 25 cc 80 grit silicon carbide, followed by another small wad of glass wool. The reactor was operated in a vertical mode in an upright furnace. The feed entered from the top. During isomerization the reactor was operated at 400° C. for one hour with a nitrogen flow rate of 20 l/h and a 1-octene flow rate as indicated in Table 4. After one hour of operation a gas sample was taken and analyzed and the results reported in Table 4. Organic liquid which had been collected in a dry ice trap for the duration of the run was also analyzed and the results reported in Table 4.

TABLE 4

| Catalyst | 1-Octene Feed | Products | | | | | | |
|---|---|---|---|---|---|---|---|---|
| | | 1-Octene | 2-Octene | 3-Octene | Aromatics | Gaseous Cracking < Products | Liquid[a] Cracking Products | n-Octane[b] |
| NaY | 5.7 g/h | 67.6 | 15.7 | 12.0 | 0.19 | 0.55 | 1.03 | 2.82 |
| Low Base | 6.1 g/h | 89.5 | 3.6 | 3.9 | 0.05 | 0.87 | 0.9 | 1.48 |
| High Base | 5.2 g/h | 47.5 | 19.1 | 32.1 | none | 0.04 | 0.0 | 1.3 |

[a]Defined as new material eluting before n-octane elution.
[b]gc analysis of feed indicated about 1.32% n-octane impurity.

As can be seen from the Table, the instant compositions show substantially no alkane make when compared to NaY zeolite. The high base composition also shows more isomerization activity than NaY zeolite and shows almost no cracking activity. Further analysis shows skeletal isomerization characteristic of acid catalysis in the sodium exchanged zeolite Y products, and not in the high base products. The lack of skeletal isomerization and cracking in the high base case confirm the virtual absence of acid sites in this basic zeolite. At the high base loadings, the instant composition gave a selectively of 99.9% or greater to olefin double bond isomerization, while the standard ion exchanged NaY gave a selectivity of less than 87%.

ILLUSTRATIVE EMBODIMENT II

Catalyst Preparation

The catalysts utilized were prepared as follows:
Fully metal exchanged zeolites Calcium-A (5A), Sodium-X (13X) and Sodium-Y (LZY-52) were used as comparative catalysts in an isomerization test and to prepare the basified catalysts of the instant invention.

CA-1

60.72 Grams of 5A zeolite pellets and 1 liter Barnstead water were stirred for approximately 16 hrs, then filtered. An additional 900 cc Barnstead water was poured through the filter funnel. The cake was then dried for 1 hour in a 150° C. vacuum oven.

A-1

20.02 Grams of the washed 5A zeolite above were impregnated with 3.93 g $Ca(NO_3)_2.4H_2O$ dissolved in 1.59 cc water. The zeolite was mixed in a pyrex dish during impregnation, and allowed to sit 9 minutes before drying 1 hour in a 150° C. vacuum oven. The zeolite was then impregnated with 4 cc water. After sitting 29 minutes, the zeolite was dried 70 minutes in a 150° vacuum oven. The powder was stirred with 100 cc 1N KOH for 1 hour, then filtered. The cake was stirred with an additional 100 cc 1N KOH for 1 hour, then filtered, and dried overnight in a 150° C. vacuum oven.

CA-2

60.91 Grams of 13X zeolite pellets were stirred overnight with 1 liter Barnstead water, then filtered. An additional 900 cc water was poured through the filter funnel. The zeolite was dried 1 hour in a 150° C. vacuum oven.

A-2

20.0 Grams of the washed 13X zeolite above were impregnated with 3.93 g $Ca(NO_3)_2.4H_2O$ dissolved in 1.59 cc Barnstead water. The zeolite was mixed in a pyrex dish during impregnation, then allowed to sit 12 minutes, and then dried 62 minutes in a 150° C. vacuum oven. The zeolite was then impregnated with 4 cc water, allowed to sit 31 minutes, then dried 65 minutes in a 150° C. vacuum oven. The dried powder was stirred with 100 CC 1N KOH for 1 hour then filtered. The cake was then stirred with an additional 100 cc 1N KOH for 1 hour, then filtered, then dried overnight in a 150° C. vacuum oven.

CA-3

130.4 Grams of LZY52 powder from Union Carbide Corporation were stirred for 1 hour with 1.5 liters water, then filtered. An additional 400 cc water was poured through the filter. The cake was dried 1 hour in a 150° C. vacuum oven.

A-3

20.03 Grams of the washed LZY52 powder above were impregnated with 3.93 g $Ca(NO_3)_2.4H_2O$ dissolved in 1.59 cc water. The zeolite was mixed in a pyrex dish during impregnation, allowed to sit 15 minutes, then dried 62 minutes in a 150° C. vacuum oven. The zeolite was then impregnated with 4 cc water, allowed to sit 31 minutes, then dried 70 minutes in a 150° C. vacuum oven. The dried powder was stirred 65 minutes with 100 cc 1N KOH, then filtered. The cake was stirred 1 hour with an additional 100 cc 1N KOH, filtered and dried overnight in a 150° C. vacuum oven.

A-4

20.02 Grams of the washed LZY52 powder above were impregnated with 4.37 g $Mg(NO_3)_2.6H_2O$ dissolved in 2.40 cc water. The zeolite was mixed in a pyrex dish during impregnation, allowed to sit 37 minutes, then dried 105 minutes in a 150° C. vacuum oven. The zeolite was then impregnated with 4 cc water, allowed to sit 24 minutes, then dried 67 minutes in a 150° C. vacuum oven. The dried powder was stirred 53 minutes with 100 cc 1N KOH, then filtered. The cake was stirred overnight with an additional 100 cc 1N KOH, filtered and dried overnight in a 150° C. vacuum oven.

The catalysts and comparative catalysts are listed in Table 4.

TABLE 4

| Catalyst No. | Isomerization Catalyst | |
|---|---|---|
| | Zeolite | Basifying Agent |
| CA-1 | 5A(Ca-A) | none |
| A-1 | 5A(Ca-A) | Ca(OH)$_2$ |
| CA-2 | 13X(Na-X) | none |
| A-2 | 13X(Na-X) | Ca(OH)$_2$ |
| CA-3 | LZY-52(Na-Y) | none |
| A-3 | LZY-52(Na-Y) | Ca(OH)$_2$ |
| A-4 | LZY-52(Na-Y) | MgO |

Catalyst Testing

Isomerization catalysts were tested in a stainless steel flow reactor measuring 14.75" in length and 0.625" in internal diameter. The reactor was packed from top to bottom as follows: a small wad of glass wool, 25 cc of 60–80 grit SiC, 14 cc of catalyst, a small wad of glass wool, 10 cc 60–80 grit silicon carbide, followed by another small wad of glass wool. The reactor was operated in a vertical mode in an upright furnace. During isomerization the reactor was heated to 275° C. under a nitrogen flow rate of about 20 liters per hour and a 1-octene flow rate of about 10 grams per hour. After one hour of operation the reaction was stopped and organic liquid trapped in an attached cold trap was analyzed and the results reported in Table 5. The temperature was then increased to 400° C. and the next isomerization test was conducted with organic liquid sample being collected for one hour of operation for analysis.

TABLE 5

Isomerization of 1-Octene

| Catalyst No. | Temp °C. | Cracking wt % | Double Bond Isom mole % |
|---|---|---|---|
| CA-1 | 400 | 4.4 | 39.5 |
| A-1 | 400 | <0.1 | 57.1 |
| CA-2 | 400 | 62.3 | 10.3 |
| A-2 | 400 | ~0.4 | 45.9 |
| CA-3 | 275 | 7.8 | 42.1 |
| CA-3 | 400 | 8.7 | 36.5 |
| A-3 | 275 | <0.2 | 12.2 |
| A-3 | 400 | 0-.6 | 49.9 |
| A-4 | 275 | ~0.01 | 59.2 |
| A-4 | 400 | <0.3 | 78.3 |

As can be seen from Table 5, the basified zeolites of the instant invention produce significantly less cracking than the corresponding non-basified zeolites and are more active.

I claim:

1. A process for the double bond isomerization of an olefin which comprises contacting said olefin with a catalyst comprising a zeolite and an alkali(ne-earth) metal compound wherein the sum of the amount of the alkali(ne-earth) metal in said compound and any metal cation exchanged in the zeolite is in excess of that required to provide a fully metal cation-exchanged zeolite.

2. The process of claim 1 wherein in the catalyst the sum of the amount of the alkali(ne earth) metal in said compound and any metal cation exchanged into the zeolite is in excess of about 1.05 times the amount required to provide a fully metal cation-exchanged zeolite.

3. The process of claim 2 wherein in the catalyst wherein the sum of the amount of the alkali(ne earth) metal in said compound and any metal cation exchanged into the zeolite is in excess of about 1.1 times the amount required to provide a fully metal cation-exchanged zeolite.

4. The process of claim 3 wherein in the catalyst the sum of the amount of the alkali(ne earth) metal in said compound and any metal cation exchanged into the zeolite is in excess of about 1.2 times the amount required to provide a fully metal cation-exchanged zeolite.

5. The process of claim 4 wherein in the catalyst the sum of the amount of the alkali(ne earth) metal in said compound and any metal cation exchanged into the zeolite is in excess of about 1.5 times the amount required to provide a fully metal cation-exchanged zeolite.

6. The process of claim 5 wherein in the catalyst the sum of the amount of the alkali(ne earth) metal in said compound and any metal cation exchanged into the zeolite is in excess of about 2 times the amount required to provide a fully metal cation-exchanged zeolite.

7. A process for the double bond isomerization of an olefin which comprises contacting said olefin with a catalyst comprising a fully metal cation-exchanged zeolite and an alkali(ne earth) metal compound.

8. The process of claim 7 wherein in the catalyst the amount of alkali(ne earth) metal present in said compound is greater than about 0.05 times the amount of alkali(ne earth) metal that would be required to provide a fully metal cation-exchanged zeolite.

9. The process of claim 8 wherein in the catalyst the amount of alkali(ne earth) metal present in said compound is greater than about 0.1 times the amount of alkali(ne earth) metal that would be required to provide a fully metal cation-exchanged zeolite.

10. The process of claim 9 wherein in the catalyst the amount of alkali(ne earth) metal present in said compound is greater than about 0.2 times the amount of alkali(ne earth) metal that would be required to provide a fully metal cation-exchanged zeolite.

11. The process of claim 10 wherein in the catalyst the amount of alkali(ne earth) metal present in said compound is greater than about 0.5 times the amount of alkali(ne earth) metal that would be required to provide a fully metal cation-exchanged zeolite.

12. The process of claim 11 wherein in the catalyst the amount of alkali(ne earth) metal present in said compound is greater than about 1 times the amount of alkali(ne earth) metal that would be required to provide a fully metal cation-exchanged zeolite.

13. The process of claims 1 or 7 wherein in the catalyst the zeolite contains micropores from about four to about twelve angstroms in diameter.

14. A process for the double bond isomerization of an olefin which comprises contacting said olefin with a catalyst prepared by impregnating a zeolite with a solution of an alkali(ne earth) metal salt wherein the sum of said alkali(ne earth) metal impregnated into the zeolite and any metal cation exchanged into the zeolite is in excess of that required to provide a fully metal cation-exchanged zeolite.

15. The process of claim 14 wherein in the process for preparing the catalyst the zeolite is first impregnated with a solution of an alkaline earth metal salt and is subsequently contacted with a precipitating agent whereby an insoluble alkaline earth metal compound precipitates within the zeolite.

16. The process of claim 15 wherein the precipitating agent is an aqueous solution of a hydroxyl-containing compound.

17. The process of claim 16 wherein the precipitating agent is an aqueous solution of an hydroxide of alkali metal, ammonium and mixtures thereof.

18. The process of claim 17 wherein the alkaline earth metal salt in the impregnating solution is not a hydroxide.

19. The process of claim 18 wherein in the process for preparing the catalyst the zeolite product is dried and calcined at a temperature ranging from about 150° C. to about 850° C.

20. The process of claim 19 wherein the calcination is carried out at a temperature ranging from about 200° C. to about 750° C.

21. The process of claim 20 wherein the calcination is carried out at a temperature ranging from about 200° C. to about 600° C.

22. A process for the double bond isomerization of an olefin which comprises contacting said olefin with a catalyst prepared by impregnating a zeolite with a molten or vaporous alkali(ne earth) metal salt which is thermally decomposable upon calcination in the presence of said zeolite and wherein the sum of said alkali(ne earth) metal impregnated into the zeolite and any metal cation exchanged into the zeolite is in excess of that required to provide a fully metal cation-exchanged zeolite and calcining the zeolite at a temperature in excess of the temperature at which the alkali(ne earth) metal salt thermally decomposes.

23. The process of claim 22 wherein in the process for preparing the catalyst the calcination is carried out at temperature ranging from about 150° C. to about 850° C.

24. The process of claim 23 wherein the calcination is carried out at temperature ranging from about 200° C. to about 750° C.

25. The process of claim 24 wherein the calcination is carried out at temperature ranging from about 200° C. to about 600° C.

26. The process of any one of claims 22–25 wherein in the process for preparing the catalyst the sum of the amount of the alkali(ne earth) metal impregnated into the zeolite and any metal cation exchanged into the zeolite is in excess of about 1.05 times the amount required to provide a fully metal cation-exchanged zeolite.

27. The process of claim 26 wherein the sum of the amount of the alkali(ne earth) metal impregnated into the zeolite and any metal cation exchanged into the zeolite is in excess of about 1.1 times the amount required to provide a fully metal cation-exchanged zeolite.

28. The process of claim 27 wherein the sum of the amount of the alkali(ne earth) metal impregnated into the zeolite and any metal cation exchanged into the zeolite is in excess of about 1.2 times the amount required to provide a fully metal cation-exchanged zeolite.

29. The process of claim 28 wherein the sum of the amount of the alkali(ne earth) metal impregnated into the zeolite and any metal cation exchanged into the zeolite is in excess of about 1.5 times the amount required to provide a fully metal cation-exchanged zeolite.

30. The process of claim 29 wherein the sum of the amount of the alkali(ne earth) metal impregnated into the zeolite and any metal cation exchanged into the zeolite is in excess of about 2 times the amount required to provide a fully metal cation-exchanged zeolite.

31. The process of any one of claims 1, 7, 14 or 22 wherein the isomerization temperature ranges from about 0° to about 500° C.

32. The process of claim 31 wherein the isomerization temperature range from about 100° C. to about 150° C.

* * * * *